US00PP37349P2

(12) United States Plant Patent
Hansen

(10) Patent No.: US PP37,349 P2
(45) Date of Patent: Mar. 31, 2026

(54) ***NEPETA* PLANT NAMED 'Catwalk Queen'**

(50) Latin Name: ***Nepeta* x *faassenii***
Varietal Denomination: Catwalk Queen

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,869

(22) Filed: Oct. 14, 2025

(51) Int. Cl.
*A01H 6/50* (2018.01)
*A01H 5/02* (2018.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP24,788 P2 * 8/2014 Hurd ..... A01H 6/50
Plt./263.1

* cited by examiner

*Primary Examiner* — Karen M Redden

(57) ABSTRACT

The new and distinct hardy perennial plant, *Nepeta* 'Catwalk Queen', has rounded, very short and compact habit with mostly upright stems. The foliage is small, serrate and fragrant. Large flowers are a periwinkle blue with persistent rosy calyces. The new plant reblooms heavily if trimmed after initial flowering.

1 Drawing Sheet

Botanical denomination: *Nepeta* x *faassenii*.
Variety designation: 'Catwalk Queen'.

BACKGROUND OF THE INVENTION

The present invention relates to a new and distinct cultivar of *Nepeta* named 'Catwalk Queen'. The new plant resulted from a cross at a wholesale perennial nursery in Zeeland, Michigan between the unnamed, proprietary hybrid known only as 20-1-1 (not patented) as the female or seed parent and the unnamed, proprietary hybrid known only as 20-1-2 (not patented) as the male or pollen parent directed by the inventor in the July of 2021. Seed was harvested in the late summer of 2021 and eventually assigned the breeder code 21-1-1 in the trial process. 'Catwalk Queen' was approved in a final evaluation in the summer of 2023 and slated for later introduction. The new plant was selected based on the compact habit, large flowers, and repeat blooming following trimming. The new plant has been asexually propagated by tip cuttings at the same nursery with the resultant plants remaining identical to the original plant, stable and true to type in successive generations.

SUMMARY OF THE INVENTION

*Nepeta* 'Catwalk Queen' is different from its parents and all other Catmint known to the inventor. In comparison to the female parent the new plant is more compact and shorter. Compared to the male parent the new plant is also shorter and more compact.

The nearest comparison varieties known to the inventor are: 'Blue Dragon' U.S. Plant Pat. No. 22,334, 'Cat's Meow' U.S. Plant Pat. No. 24,472, 'Cat's Pajamas' U.S. Plant Pat. No. 31,127, 'Kitten Around' U.S. Plant Pat. No. 30,940, 'Novanepjun' U.S. Plant Pat. No. 23,074, more commonly known as 'Junior Walker', 'Picture Purrfect' U.S. Plant Pat. No. 34,502, and 'Summer Magic' U.S. Plant Pat. No. 27,090.

Compared with 'Novanepjun' the new plant is more compact with smaller leaves, larger flowers, and shorter habit. Compared with 'Walker's Low' (not patented) the new plant is less than one-half the landscape size and is more compact with larger flowers. In comparison to 'Blue Dragon', 'Cat's Meow', and 'Summer Magic' the new plant is more compact and shorter than each cultivar and has larger flowers. 'Kitten Around' has smaller flowers and is more rounded and less flat in habit. 'Catwalk Queen' flowers earlier than 'Cat's Meow', 'Kitten Around', and 'Novanepjun'. 'Cat's Pajamas' is slightly larger in habit and has smaller flowers. 'Picture Purrfect' has a looser habit and smaller flowers.

The present invention has not been evaluated under all possible environmental conditions. The phenotype may vary with changes in the environment such as light, temperature, water and nutrient availability, etc. without a change in the genotype of the plant. *Nepeta* 'Catwalk Queen' is unique from all other catmint known to the inventor in the following combined traits:

1. The habit is low, rounded, very short and compact with mostly upright stems.
2. Foliage is small and fragrant with serrate teeth.
3. Large flowers are periwinkle blue with persistent rosy-purple calyces.
4. Plant reblooms heavily if trimmed after initial flowering.

BRIEF DESCRIPTION OF THE DRAWINGS

The photographs of the new plant *Nepeta* 'Catwalk Queen' are of a two-year-old plant in a full-sun, trial garden in Zeeland, Michigan and demonstrate the unique aspects of the new plant. The colors are as accurate as reasonably possible with color reproductions. Ambient light: spectrum, temperature, source and direction may cause the appearance of minor variation in color.

DETAILED PLANT DESCRIPTION

Figure 1:
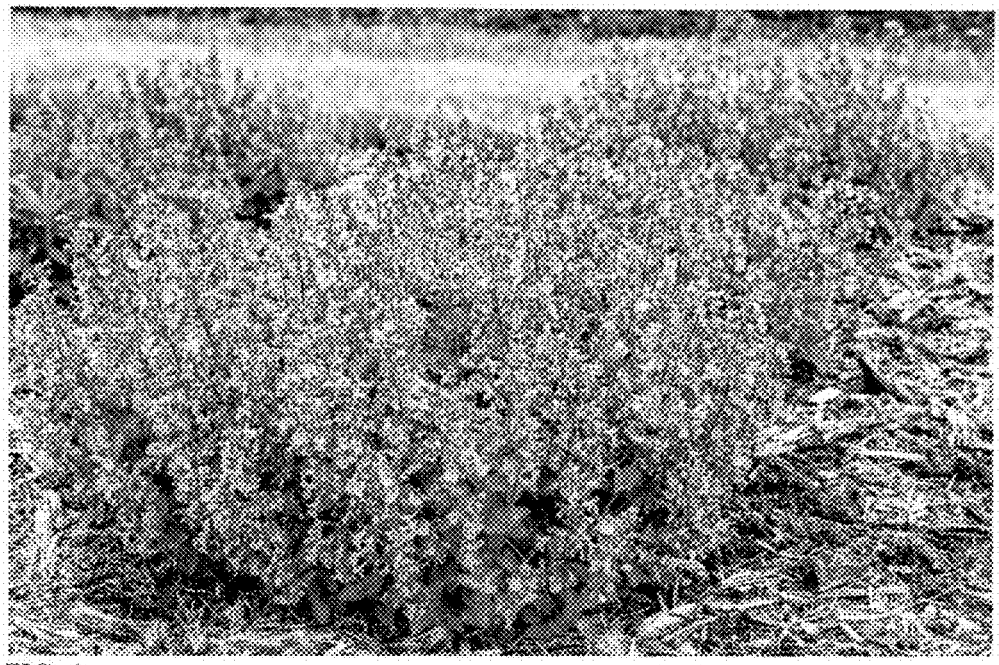
FIG. 1 shows the overall habit of *Nepeta* 'Catwalk Queen'.
Figure 2:
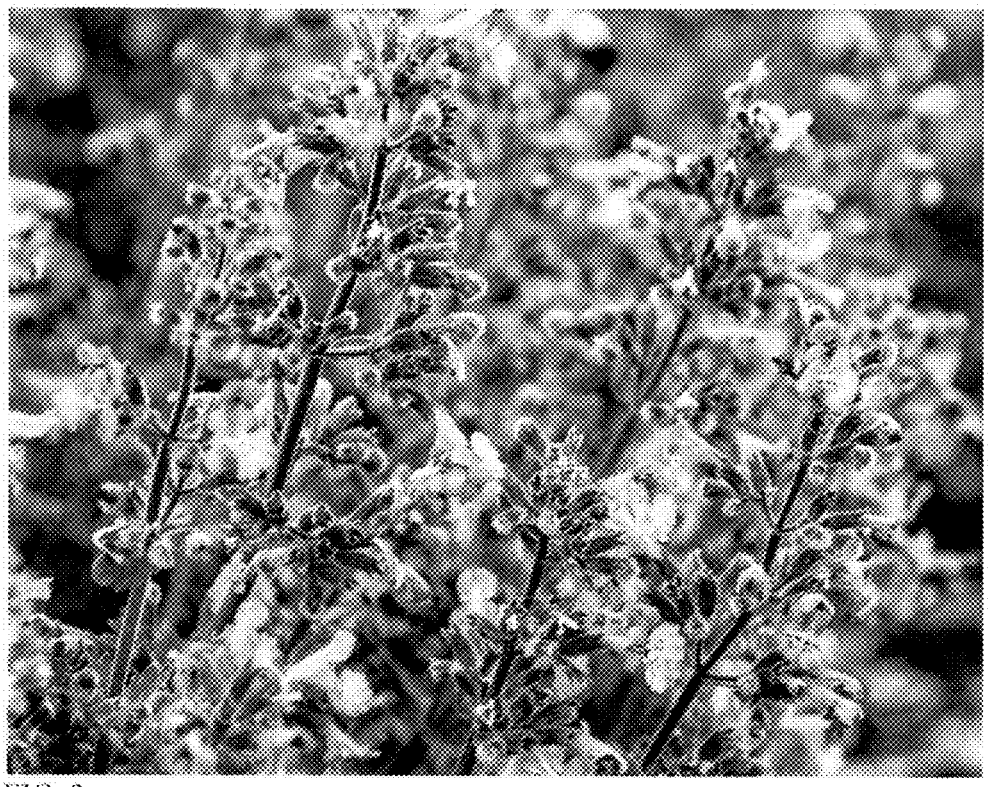
FIG. 2 shows a close-up of the flowers, buds and stems.

The following descriptions are based on a two-year old plant of *Nepeta* 'Catwalk Queen' grown in a full-sun trial garden in sandy loam with supplemental water and fertilizer as needed. The color references are based on the 2015 edition of The Royal Horticultural Society Colour Chart except where common dictionary terms are used. The new plant has not been observed under all possible environments. The phenotype may vary slightly with different environmental conditions, such as temperature, light, fertility, moisture and maturity levels, but without any change in the genotype.

Parentage: 21-1-1 as the female or seed parent, the male or pollen parent was 21-1-2;

Plant habit: Herbaceous perennial; short mounding to about 29 cm tall and 62 cm wide at the base in flower;

Growth: Rapid; time to initiate roots at 23° C. about one week; finishing in a standard #1-15 cm container in about 8 to 10 weeks from rooted 25 mm plug;

Root: Fine, freely branching; color nearest RHS 158D depending on soil type and nutrient content;

Leaves: Opposite; simple; ovate; rugose and micro-puberulent on both abaxial and adaxial surfaces; margins serrate with about 11 teeth per side; finely puberulent on abaxial and adaxial surfaces; apex broadly acute; base cordate; blade size to about 31 mm long and 22 mm wide, average about 22 mm long and 17 mm across;

Leaf color: Young expanding adaxial nearest RHS 137A, young expanding abaxial between RHS N138B and RHS 138A; mature adaxial between RHS 137B and RHS 137A, mature abaxial between RHS 137B and RHS 147B;

Foliage fragrance: Foliage and stem herbal fragrance;

Venation: Longitudinal; impressed on adaxial surface and ribbed on abaxial surface;

Vein color: Adaxial nearest RHS NN137A and abaxial between RHS 146B and RHS 146;

Petiole: Micro-puberulent adaxial and abaxial; slightly concavo-convex; to about 6 mm long and 1.7 mm across at base; average about 4 mm long and about 1.5 mm across;

Petiole color: Adaxial and abaxial between RHS 147C RHS 146D;

Stem: Micro-puberulent; quadrangular; to about 26 cm long and 3 mm across at base; about 80 stems per plant; lightly branched; 8 branches per stem, branches to about 15 cm long and 1.5 mm across at base;

Stem color: Between RHS 138B and RHS 138A;

Internodes: Average about 2 cm apart with greatest distance in the middle of the stem; about 8 nodes per stem before terminal flowers, branched in the lower 5 nodes;

Internode color: Between RHS 138B and RHS 138A;

Inflorescence: Cymosely clustered with many flowers either sessile, with short pedicel, or branched at verticillasters in the 7 upper nodes; about 6 to 25 flowers per node and about 40 to 90 flowers per inflorescence stem or peduncle;

Peduncle: Mainly vertical; flower portion in distal 15 cm tall and 5 cm wide;

Pedicel: Rare; cylindrical and short when present; to about 1 mm long and 0.5 mm diameter;

Pedicel color when present: Between RHS N77C and RHS N77D;

Flower bud: Arcuate clavate; apex rounded; base attenuate; about 13 mm long, 5 mm tall, and 3 mm wide near apex one day prior to opening; abaxial surface micro-puberulent;

Flower bud color: Dorsal petal portion between RHS N88C and RHS 88D and ventral portion between RHS NN155D and RHS 85D; calyx portion nearest abaxial nearest RHS 137C distally and nearest RHS 147D proximally with veins in high light and dorsal moderate blush nearest RHS N77A;

Flowers: Zygomorphic; perfect; bilabiate; sympetalous with basal 13 mm fused; synsepalous; lips opening to form about 80-degree angle to each other; 19 mm long and 14 mm tall and 8 mm across broadest face; in verticillasters;

*Upper lip*.—With two lobes; puberulent on basal two-thirds of abaxial surface, glabrous distally and adaxial; lobes about 5 mm long from fusion and 3.5 mm wide above fusion; lobes with rounded apex and entire margin; total size of lip about 19 mm long and about 7 mm wide at fusion.

*Lower lip*.—Consisting of three lobes; center and largest lobe concaved with rounded emarginate apex, crenate margin, and auriculate base; two side lobes with rounded apices and entire margin; center lobe to 8 mm long from fusion and 8 mm across natural spread and 11 mm across when flattened; side lobes 2 mm long from fusion and 4 mm across; puberulent abaxial, glabrous adaxial except pubescent tuft of white hairs nearest NN155D about 1 mm long outside fusion of two lips.

*Corolla tube*.—To about 14 mm long and 5 mm tall and 2 mm across at fusion.

*Petal initial color*.—Adaxial face upper lip and lower lip side lobes nearest RHS N87C, and lower lip middle lobe between RHS 91D and RHS 91C near the center with to 1 mm spots of nearest RHS 83B, and with marginal rim nearest RHS 91A; adaxial tube distally nearest RHS N82D, and proximally between RHS 85D and RHS NN155C, with spots about 0.3 mm to 1 mm diameter in proximal tube mouth nearest RHS 83B on the inside lower lip; abaxial upper face between RHS N82C and RHS N82D; abaxial tube distally nearest RHS N82D and proximally between RHS 85D and RHS NN155C.

Calyx: Synsepalous, 5-merous fused into tube in basal 4.5 mm and separated in distal 3 mm; about 7.5 mm long and 3.5 mm diameter;

Sepals: Five; acute apex, base fused; with about 3 conspicuous longitudinal veins; puberulent adaxial, glabrous abaxial; persistent; about 7.5 mm long and 1 mm across at fusion;

Sepal color: Adaxial distal portion nearest RHS 137C, proximally nearest RHS 145D with veins nearest RHS 137C; abaxial nearest RHS 137C distally and nearest RHS 147D proximally with veins in high light and dorsal moderate blush nearest RHS N77A;

Gynoecium: Single compound ovary with two carpels, single gynobasic style, and bifurcate stigma;

*Style*.—Cylindrical; glabrous; lustrous; about 13 mm long and 0.5 mm diameter; color nearest RHS N81C.

*Stigma*.—Bifid in distal 1 mm to sharply acute apex; color between RHS N92B and RHS 93A.

*Ovary*.—Four-lobed, each lobe ovoid, about 1 mm long and 0.5 mm across, ovary color between RHS 145A and RHS N144D.

Androecium: Four; in two pairs;

*Filaments*.—Four; cylindrical; glabrous; lustrous; to about 15 mm long and 0.2 mm diameter, adnate to adaxial petals in basal 11 mm, free in distal 4.0 mm; color nearest RHS N82D.

*Anthers*.—Oblong ellipsoidal; dorsifixed; longitudinal; to about 1 mm long and 0.5 mm diameter; color nearest RHS N92C.

*Pollen*.—Abundant; color nearest RHS NN155B.

Flowering period: In Western Michigan beginning early June for four weeks and repeating into October if trimmed back; individual flowers remain open for up to three days;

Flower fragrance: None detected;

Flower aspect: Outwardly;

Fruit and seed: Rare under natural pollination; one to two nutlets; flattened globose; to about 2 mm diameter and 0.7 mm thick; nearest RHS 200B;

Pest and disease susceptibility: No resistance beyond that which is typical for *Nepeta* but susceptible to *Ersiphe* (powdery mildew) and *Pseudomonas* (leaf spot).

I claim:

1. The new and distinct hardy perennial *Nepeta* plant named 'Catwalk Queen' as herein described and photographed.

* * * * *